United States Patent [19]

Croll

[11] Patent Number: 4,780,083

[45] Date of Patent: Oct. 25, 1988

[54] COMPOUND AND DENTAL APPLICATOR FOR ENAMEL REMOVAL

[76] Inventor: Theodore P. Croll, 685 S. Chubb Dr., Doylestown, Pa. 18901

[21] Appl. No.: 811,447

[22] Filed: Dec. 20, 1985

[51] Int. Cl.$^4$ ............................................. A61K 5/00
[52] U.S. Cl. ................................... 438/216; 433/142; 424/49
[58] Field of Search .................. 433/80, 141, 142, 216, 433/88; 132/93; 604/1, 2, 93, 289, 309; 424/55, 49

[56] References Cited

U.S. PATENT DOCUMENTS

| | | | |
|---|---|---|---|
| 364,916 | 6/1887 | Goldsmith | 401/52 |
| 431,713 | 7/1890 | Whaley | 132/93 |
| 1,632,686 | 6/1927 | Withycombe | 604/289 |
| 2,623,003 | 12/1952 | Friedlob et al. | 433/216 |
| 3,718,973 | 3/1973 | Slater et al. | 433/80 |
| 3,803,301 | 4/1974 | Cordon et al. | 424/49 |
| 3,995,024 | 11/1976 | Hawking | 424/55 |
| 4,100,269 | 7/1978 | Pader | 424/55 |
| 4,108,981 | 8/1978 | Muhler et al. | 424/55 |
| 4,170,635 | 10/1979 | Barth | 424/55 |
| 4,411,623 | 10/1983 | Axelsson | 433/80 |

FOREIGN PATENT DOCUMENTS 0486266 9/1952 Canada .................................. 433/88

OTHER PUBLICATIONS

Bailey, Ronald W. and Arden G. Christen, "Bleaching of Vital Teeth Stained with Endemic Dental Fluorosis", *U.S., O.M. and O.P.*, pp. 871–878, 12/1968.

McCloskey, Robert J., "A Technique for Removal of Fluorosis Stains", *JADA*, vol. 109, pp. 63–64, 7/1984.

Chandra, Satish and T. N. Chawla, "Clinical Evaluation Of The Sandpaper Disk Method For Removing Stains From Teeth", *JADA*, vol. 90, pp. 1273–1276, 6/1975.

Colon, P. G., "Removing Fluorosis Stains From Teeth", *Quintessence International*, vol. 6, pp. 1–5, 6/1971.

*Primary Examiner*—John J. Wilson
*Assistant Examiner*—Adriene J. Lepiane
*Attorney, Agent, or Firm*—Gregory J. Gore

[57] ABSTRACT

This invention relates to dentistry, and more particularly to cosmetic dentistry, where for aesthetic objectives it is desirable to remove a small amount of the patient's tooth enamel to modify tooth color. A procedure is described using an applicator and compound which provides accelerated treatment time in stripping away a sufficient amount of the outer layer of the tooth enamel to provide the necessary tooth color modification. The applicator has two functional ends. One end has a containment pocket for holding the compound, and a second end for high pressure scouring of the tooth enamel. The compound comprises an enamel softening acid, such as hydrochloric acid, in the concentration range of between 6%–16% in combination with an abrasive particulate material. The abrasive material should have a hardness greater than 6.0 as measured on the Mohs hardness scale for greatest effectiveness.

8 Claims, 1 Drawing Sheet

COMPOUND AND DENTAL APPLICATOR FOR ENAMEL REMOVAL

FIELD OF INVENTION

This invention relates to dentistry, and more particularly to cosmetic dentistry, where for aesthetic objectives it is desirable to remove a small amount of the patient's tooth enamel to modify tooth color.

BACKGROUND OF INVENTION

In most cases, the procedure for color correcting intrinsic tooth staining resulting from developmental enamel hypoplasia or altered mineralization of the enamel structure is to bond layers of resin veneer to the tooth to mask the defective enamel. A particular type of enamel discoloration, namely fluorosis staining, has been treated in ways which are related to but not anticipatory of the instant invention. These treatments include: mechanically grinding or sanding the enamel away, chemically dissolving the enamel or, lastly, by the technique of bleaching with a solution containing concentrated hydrogen peroxide.

Mechanical means of enamel removal employ grinding or sanding in conjunction with rotary power tools to speed the process. While this method indeed removes enamel structure, there is little fine control over the spinning powered cutting instrument and often the enamel is removed in an uneven fashion. In addition, the slightest error with the powered hand tool can cause significant damage deep into the enamel structure. This purely mechanical method is quite time consuming and can cause patient discomfort due to friction heating of the hard tooth structure by the rotating device.

Bleaching techniques have shown to be extremely time consuming, requiring numerous patient visits, and giving unpredictable results. The process is also often used in combination with heating of the tooth which can be painful to the patient and difficult to adequately administer. In addition, the dental pulp (nerve of the tooth) can be damaged if heated excessively.

A purely chemical approach to tooth enamel dissolution for enamel removal requires the use of hydrochloric acid in a strong concentration of 18% to 36% in solution. This method requires the acid be in contact with the tooth up to 10 minutes and also there is no ability to localize the treatment to a particular area of the tooth. The prior art technique of bleaching had occasionally used hydrochloric acid as a component of the solution, or in a separate step to the procedure, but in all reported cases, the hydrochloric acid used as an etching agent only. Abrasion was to be avoided.

In summary, the problems with prior art methods of removing enamel are that; they are time consuming, cause patient discomfort, are inadequate for intrinsic staining other than fluorosis, lack the adequate control to localize the treatment to specific areas of the tooth, and are inherently unsafe because dangerous acidic solutions are of strong concentration and if used in combination with powered rotary hand tools could easily cause uncontrolled scattering of harmful acid covered particles.

SUMMARY OF THE INVENTION

Many different types of human dental enamel discoloration once thought to be stain which penetrates deep into the tooth structure is actually a superficial staining of the outer enamel layer. In order to solve prior art problems of enamel removal to eliminate the stained areas and therefore correct the discoloration of teeth, the present invention discloses a controlled procedure for stripping away a clinically insignificant amount of enamel structure and thus permanently eradicating the enamel discoloration defect. This procedure provides, for the first time, a combination of both mechanical action and chemical action working on the enamel simultaneously, in one step. This procedure gives an astonishingly fast result without the need for powered rotary tools Surprisingly, the instant procedure accelerates the known enamel removal portion of the treatment time by approximately ten-fold. This is achieved by including a highly abrasive cutting ingredient to an acid solution and by applying the dual compound to the tooth under high pressure in a controlled, manual scouring motion. According to this procedure, the acid compound is in contact with the tooth for only a very short time (about 60–90 seconds) during the entire treatment. Also, depending upon applicator pressure, the acid concentration need only be a solution in the range of 6% to 16%. Here, the action of the acid is not so much to dissolve the enamel as it is to soften it. The cutting action of the abrasive material simultaneously abrades away the softened enamel. There may also be included a third element which serves as a suitable carrier to maintain appropriate proportions of these two elements in the form of a thick paste.

The compound is applied to the tooth by a rigid applicator which can withstand pressure of at least 50 PSI at point of contact. In conjunction with this procedure, a new and surprisingly effective applicator has been devised. This applicator has two functional ends. One end provides a containment pocket for carrying the stain removal compound to the tooth and holding it during the application procedure. The pocket helps confine the compound to the treatment area during the vigorous motion of the applicator. The second end has a pointed tip so that, once applied to the tooth, the compound can be scoured under high pressure into a very localized area of the enamel.

Acid compounds are inherently dangerous but this procedure achieves a high degree of safety because lower concentrations of acid are sufficient and the need for rotating power tools is eliminated. In conjunction with the applicator described herein, this procedure provides greater control of the compound and hence increased safety for both patient and physician. The procedure has been proven surprisingly effective and eliminates many additional steps of prior art enamel treatment. Unlike others, this procedure has also shown to be very effective regarding all types of tooth staining, including; colored lesions, yellow and brown stains, bright white spots, diffuse paper white flecking, and all types of multicolored enamel defects, so long as such defects are confined to the superficial enamel region. Applicant's invention is also the discovery that many of the different types of enamel discoloration once thought to be deep stains are actually rather superficial in a vast majority of cases. The heretofore unknown source of the problem is part of the reason why the results of this compound used on non-fluorosis type stains is so surprising and unexpected.

Therefore, an object of the instant invention is to provide an improved dental procedure to color correct teeth by removal of a small amount of the tooth enamel structure.

Other objects of the instant invention are to provide a dental procedure and dental compound applicator which allows for fast, safe, and permanent removal of any superficial, intrinsic tooth stain without patient discomfort. It is a further object of the instant invention to provide for the removal of the enamel from living human teeth which preserves the natural anatomical contour of the tooth.

DESCRIPTION OF PREFERRED EMBODIMENT

Although there may be various modifications of the elements generally described herein as constituting the compound to be used in this novel procedure, it has been found that an aqueous solution of 9% hydrochloric acid mixed with silicon carbide makes a suitable compound combined at a volumetric ratio of approximately 2:1, respectively. The silicon carbide should be ground within a range of 100 to 250 mesh grade. Other abrasives may be used, however, it should have a hardness of at least 6.0 on the Mohs hardness scale. Both quartz and diamond are alternative abrasives, however, silicon carbide is very hard and also very inexpensive. Acids shown to have enamel softening properties include; hydrochloric nitric, citric, chromic and phosphoric. However, hydrochloric acid has shown to be superior for this dental compound. This compound using a 9% hydrochloric acid solution is approximately 1.5% HCL by weight.

The procedure is to be carried out by first isolating the teeth to be treated by a rubber dam and to seal around the margins of the tooth or teeth with copal varnish. Next, the acid/abrasive compound is ground into the labial surface of the enamel by means of a hand applicator in the stained areas of the tooth. The scrubbing action of the applicator, especially when used with high pressure, digs the sharp particles of silicon carbide into the softened enamel and abrades away the outer layer of the enamel very quickly. Intermittent rinsing during the scouring process should be employed to aid observation. In seconds, the stains will begin to disappear. The total scouring time should not exceed more than approximately 60–90 seconds. The scouring process is continued until either the stains have been removed or the dentist observes that too much enamel is being removed and the stain is too deep for this procedure.

After the stain has been removed, the tooth is covered with a solution of sodium fluoride gel such as Prevident (R) which is applied to the tooth for approximately 60 seconds. After the fluoride treatment, the tooth is finely polished with a dental prophylaxis paste and rubber cup using a hand piece rotating at approximately 2,000 RPM. The tooth is then rinsed and the rubber dam removed. A tooth or pair of adjacent teeth may be treated in this manner in approximately 10–15 minutes. This stain removal can be accomplished in a single office visit.

Figure 1:
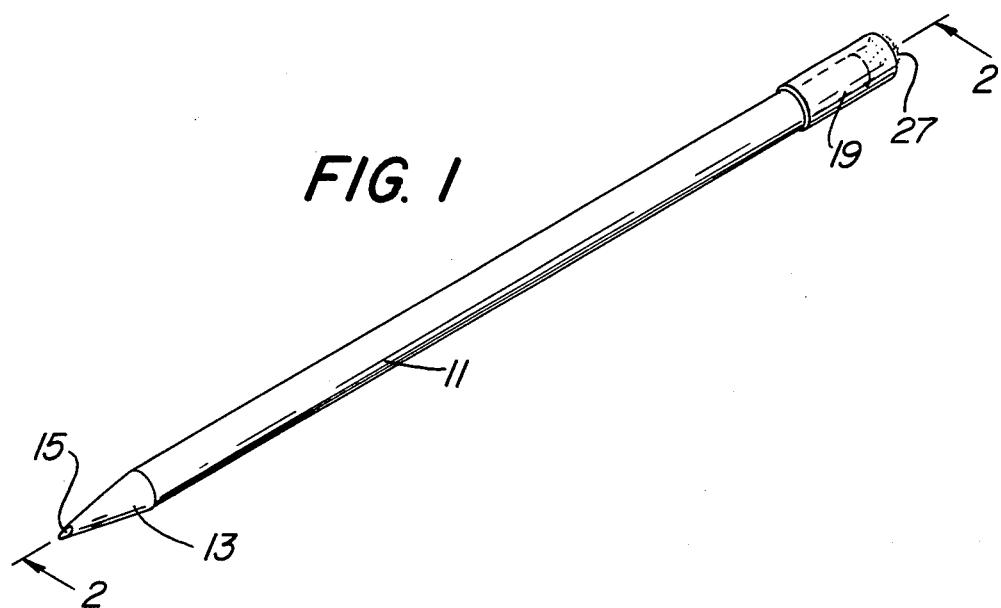
FIG. 1 shows an isometric view of the applicator.
Figure 2:
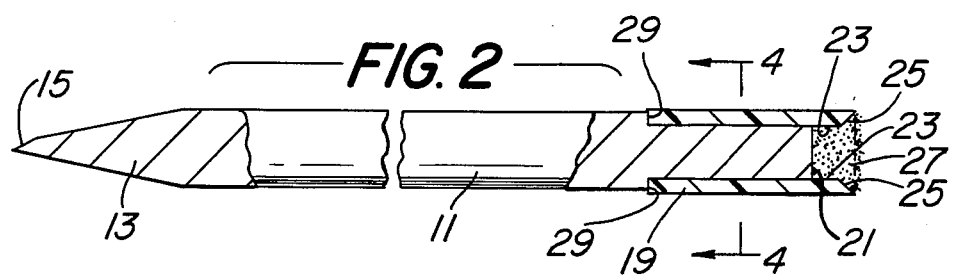
FIG. 2 shows sectional view of FIG. 1 along line 2—2 showing more details of the first end of the applicator.
Figure 3:
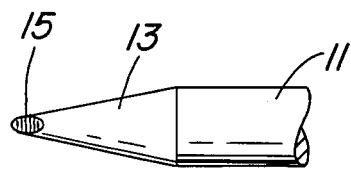
FIG. 3 is a top view showing details of the pointed tip.
Figure 4:
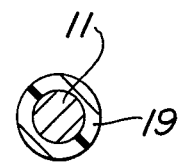
FIG. 4 is a sectional end view of FIG. 2 along line 4—4.

In conjunction with this procedure, a simple and very effective applicator has been devised to aid in the controlability and high pressure application of the stain removal compound. Referring to FIG. 1, this applicator comprises a cylindrical wooden shaft 11 which is pointed at a first end 13 and which contains a transparent, resilient, sleeve 19 projecting from the second end creating a containment pocket. Referring now to FIG. 2, the endface 21 of the applicator shaft 11 which creates the back wall of the containment pocket 17 has a flat face and this surface is used to apply the compound. Sleeve 19 or shaft 11 may be angled to facilitate the use of the applicator. Bevelled edges 25 allow the lip of the containment pocket to conform to the curved surface of the tooth. Referring now to FIG. 3, tapered tip 13 contains truncated elliptical portion 15 to provide an applicator surface for small area and spot application. Referring now to FIG. 4, the end view taken from FIG. 2 shows the circular configuration of resilient sleeve 19 which is fitted about shaft 11 which has a reduced diameter at one end.

In practice, the physician's assistant inserts the containment pocket end of the applicator into a quantity of the stain removal compound and once extracted therefrom the containment pocket will be filled with a fixed amount of the compound 27 (see FIG. 2) because of its cohesive nature. The dental assistant then hands the applicator to the physician who applies the compound to the tooth by pressing the containment pocket against it. As the containment part of the applicator is forced against the tooth, the resilient nature of the sleeve 19 causes the pocket sidewall 23 to deform and allows the endface 21 to press the stain removal compound into the enamel surface of the tooth. During the scouring motion of the applicator, the sleeve sidewalls contain the possible lateral scattering of acid compound particles. Also, because the sleeve on this end of the applicator is transparent, the physician can see the action of the compound against the surface of the tooth as it is being applied. In this way, the applicator serves the purposes of measurement, transportation, and location of the compound against the tooth, all in one device.

The sleeve 19 is preferably made of clear plastic material which is easily deformable. It is fitted on the end of the shaft abutting a shoulder 29 which is formed by reducing the shaft diameter. This sleeve extends from the end of the shaft endface 21 by approximately ⅛". The applicator also has a second, pointed end which is configured to enable the physician to localize the scouring of the acid compound to a very small area of the tooth and to increase the application pressure. In this way, enamel is only removed from the areas where it need be. This also greatly reduces treatment time.

Another reason for the accelerated treatment time is that the hydrochloric acid is used to soften the enamel rather than to dissolve it. This allows a weaker concentration to be used for a shorter amount of time. Furthermore, after the acid/abrasion scouring, the condition of the remaining enamel is close to its normal luster. Therefore, the final fine polishing step can be performed very quickly.

The preferred form for materials of this procedure is a treatment kit for dentists. This kit should include a quantity of hydrochloric acid to form a treatment paste, a fluoride gel, an applicator, and a prophylaxis paste for the final polishing step.

It should be understood that there may be many modifications and adaptations to the embodiment of the invention outlined herein and still fall within the scope and spirit of the invention. It is not, therefore, intended that the specific embodiments described herein be a limitation upon the scope of the invention which shall be determined by the appended claims and their legal equivalents.

What is claimed is:

1. A tooth compound for removing enamel from living human teeth, comprising;

hydrochloric acid of an enamel-dissolving concentration and abrasive particulate matter having a hardness of greater than 6.0 measured on the Mohs hardness scale.

2. The tooth compound of claim 1 further described in that said acid is hydrochloric acid in an aqueous solution in the concentration range of 8% to 16%.

3. The tooth compound of claim 2 further including a carrier substance so that said tooth compound forms a paste.

4. The tooth compound of claim 1 wherein said abrasive particulate matter is from the group consisting of: quartz, silicon carbide and diamond.

5. A procedure for removing enamel to remove stains, including white spots, from living human teeth by simultaneous chemical-mechanical abrasion, comprising of steps of:

a. frictionally scouring a tooth compound comprising hydrochloric acid of a concentration to quickly dissolve enamel and abrasive particulate matter having a Mohs hardness of greater than 6.0 into the surface of the tooth with a dental applicator by direct mechanical pressure, b. rinsing the tooth compound from the tooth, c. applying fluoride to the tooth, and d. polishing the tooth to restore natural luster.

6. The procedure of claim 5 wherein said tooth compound does not contain hydrogen peroxide or other bleaching agents.

7. A procedure for treating indemic tooth staining, including white spots, such as fluorosis of enamel hypoplagia in living human teeth, comprising;

frictionally scouring by direct mechanical pressure a tooth compound comprising concentrated hydrochloric acid and an abrasive particulate matter onto the surface of said teeth with a dental applicator, said treatment procedure accomplishing stain removal by a controlled removal of tooth enamel by simultaneous chemical-mechanical abrasion.

8. The procedure of claim 7 wherein said tooth compound does not contain hydrogen peroxide or other bleaching agents.

* * * * *